US007686451B2

(12) United States Patent
Cleveland

(10) Patent No.: US 7,686,451 B2
(45) Date of Patent: Mar. 30, 2010

(54) EXPLICIT RAYTRACING FOR GIMBAL-BASED GAZEPOINT TRACKERS

(75) Inventor: Dixon Cleveland, Annandale, VA (US)

(73) Assignee: LC Technologies, Inc., Fairfax, VA (US)

( * ) Notice: Subject to any disclaimer, the term of this patent is extended or adjusted under 35 U.S.C. 154(b) by 625 days.

(21) Appl. No.: 11/396,596

(22) Filed: Apr. 4, 2006

(65) Prior Publication Data

US 2006/0239670 A1  Oct. 26, 2006

Related U.S. Application Data

(60) Provisional application No. 60/667,672, filed on Apr. 4, 2005.

(51) Int. Cl.
*A61B 3/14* (2006.01)
(52) U.S. Cl. .................................... 351/210
(58) Field of Classification Search .................. 351/210
See application file for complete search history.

(56) References Cited

U.S. PATENT DOCUMENTS

| 5,090,797 | A | * | 2/1992 | Cleveland et al. ........... 351/210 |
| 5,912,721 | A | * | 6/1999 | Yamaguchi et al. ......... 351/210 |
| 5,956,122 | A | * | 9/1999 | Doster ........................ 351/210 |
| 6,553,281 | B1 | * | 4/2003 | Liu ............................. 700/302 |
| 6,886,137 | B2 | * | 4/2005 | Peck et al. .................. 715/785 |
| 2004/0174496 | A1 | * | 9/2004 | Ji et al. ....................... 351/209 |
| 2005/0175218 | A1 | * | 8/2005 | Vertegaal et al. ............ 382/103 |
| 2006/0109242 | A1 | * | 5/2006 | Simpkins .................... 345/156 |

\* cited by examiner

*Primary Examiner*—Jessica T Stultz
*Assistant Examiner*—Mahidere S Sahle
(74) *Attorney, Agent, or Firm*—John R. Kasha; Kasha Law LLC

(57) ABSTRACT

One embodiment of the present invention is a method for computing a first gaze axis of an eye in a first coordinate system. A camera is focused on the eye and moved to maintain the focus on the eye as the eye moves in the first coordinate system. A first location of the camera in the first coordinate system is measured. A second location of the eye and a gaze direction of the eye within a second coordinate system are measured. A second gaze axis within the second coordinate system is computed from the second location and the gaze direction. The first gaze axis is computed from the second gaze axis and the first location using a first coordinate transformation.

16 Claims, 8 Drawing Sheets

EXPLICIT RAYTRACING FOR GIMBAL-BASED GAZEPOINT TRACKERS

CROSS-REFERENCE TO RELATED APPLICATION

This application claims the benefit of U.S. Provisional Patent Application Ser. No. 60/667,672 filed Apr. 4, 2005, which is herein incorporated by reference in its entirety.

This invention was made with Government support under NIH/SBIR Grant number 2 R44 HD29980-03 awarded by U.S. Department of Health and Human Services. The Government has certain rights in the invention.

FIELD OF THE INVENTION

Embodiments of the present invention relate to video eyetrackers. More particularly, embodiments of the present invention relate to video eyetracking systems and methods that accurately predict a user's gazepoint, while accommodating for significant movement of the user's head.

BACKGROUND INFORMATION

Video eyetrackers are camera-based devices that observe a person's eyes and predict the point in space where the person is looking. A key limitation of most video eyetrackers today is that the user has to hold his head fairly still.

In view of the foregoing, it can be appreciated that a substantial need exists for systems and methods that accurately account for head motion while video eyetracking.

BRIEF SUMMARY OF THE INVENTION

One embodiment of the present invention is a system for computing a first gaze axis of an eye in a first coordinate system. A camera focuses on the eye and moves to maintain the focus on the eye as the eye moves in the first coordinate system. A gimbal is connected to the camera. The gimbal is used to move the camera. A processor is connected to the camera and the gimbal such that the processor controls the focus of the camera, controls movement of the gimbal, and measures a first location of the camera in the first coordinate system. The processor measures a second location of the eye and a gaze direction of the eye within a second coordinate system. The processor computes a second gaze axis within the second coordinate system from the second location and the gaze direction. The processor computes the first gaze axis from the second gaze axis and the first location of the eye with the first coordinate system using a first coordinate transformation.

Another embodiment of the present invention is a method for computing a first gaze axis of an eye in a first coordinate system. A camera is focused on the eye and moved to maintain the focus on the eye as the eye moves in the first coordinate system. A first location of the camera in the first coordinate system is measured. A second location of the eye and a gaze direction of the eye within a second coordinate system are measured. A second gaze axis within the second coordinate system is computed from the second location and the gaze direction. The first gaze axis is computed from the second gaze axis and the first location using a first coordinate transformation.

Another embodiment of the present invention is a system for determining a three-dimensional location and orientation of an eye within a camera frame of reference. This system includes a camera, an illuminator, and a processor. The camera captures an image of the eye. The illuminator generates a reflection off of a corneal surface of the eye. The processor computes a first two-dimensional location of a pupil reflection image and a corneal reflection image from the image of the eye. The processor predicts a second two-dimensional location of a pupil reflection image and the corneal reflection image as a function of a set of three-dimensional position and orientation parameters of the eye within the camera frame of reference. The processor iteratively adjusts the set until the first two-dimensional location is substantially the same as the second two-dimensional location. The set of three-dimensional position and orientation parameters of the eye within the camera frame of reference then define the three-dimensional location and orientation of the eye.

Figure 1:
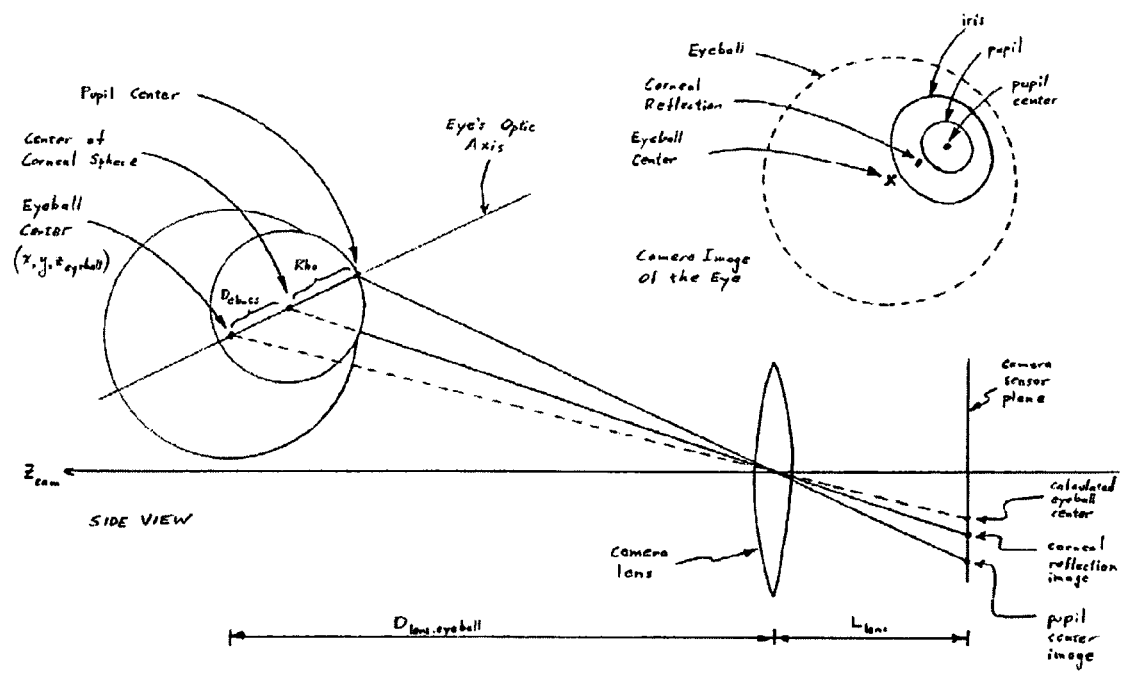
FIG. 1 is a schematic diagram showing a location of an eyeball center with respect to a pupil center and corneal reflection.

Before one or more embodiments of the invention are described in detail, one skilled in the art will appreciate that the invention is not limited in its application to the details of construction, the arrangements of components, and the arrangement of steps set forth in the following detailed description or illustrated in the drawings. The invention is capable of other embodiments and of being practiced or being carried out in various ways. Also, it is to be understood that the phraseology and terminology used herein is for the purpose of description and should not be regarded as limiting.

DETAILED DESCRIPTION OF THE INVENTION

Embodiments of systems and methods for video eyetracking that account for head motion are described in this detailed description of the invention. In this detailed description, for purposes of explanation, numerous specific details are set forth to provide a thorough understanding of embodiments of the present invention. One skilled in the art will appreciate, however, that embodiments of the present invention may be practiced without these specific details. In other instances, structures and devices are shown in block diagram form.

Furthermore, one skilled in the art can readily appreciate that the specific sequences in which methods are presented and performed are illustrative and it is contemplated that the sequences can be varied and still remain within the spirit and scope of embodiments of the present invention.

To obtain accurate gazepoint tracking, an exemplary eyetracking system called an "eyegaze system," uses a camera with a telephoto lens that obtains a high-resolution image of the user's eye. The telephoto lens, however, has a small field of view, so it becomes the user's responsibility to keep his head within that small field of view.

Some users have trouble keeping their heads this still. One embodiment of the present invention is an eyetracking system that allows eyetracker users to move their heads freely.

Objectives

Conventional eyetracking systems typically have a permissible head range of approximately 1.5 inches side-to-side, 1.2 inches up and down, and 1.5 inches back and forth. In this invention the desired range of motion is, for example, 18 inches side to side, ten inches forward and back, and eight inches up and down. One embodiment of the present invention is an eyefollower that can be used to increase the eyegaze system's tolerance to head motion by a factor of 1000, about an order of magnitude in each direction.

An important underlying eyetracker performance goal is to minimize the eyefollower's impact on the eyegaze system's overall gazepoint-tracking accuracy. Accordingly, an embodiment of this invention keeps the additional gazepoint tracking error induced by the eyefollower to less than 20% of the original gazepoint tracking error obtained by a fixed camera system without the eyefollower.

Approach

It is well known that a wider-angle lens may be used to increase a system's tolerance to head motion, thus increasing the camera's field of view. A wider field of view, however, can result in decreased resolution of the eye image, which in turn results in decreased accuracy of the gazepoint tracking. Even with higher resolution cameras and frame grabbers, the wider angle lenses only allow the tolerance to head motion to increase by a factor of about 4, far less than the desired 1000 fold increase.

In an embodiment of the present invention, an eyefollower is used to increase tolerance to head motion. As the user moves his head, a gimbal mechanism automatically points the camera to keep the eye centered within the camera image, and an autofocus mechanism keeps the lens focused on the eye. This approach is similar to the human eye: when we wish to look at something, we rotate our eyes to aim the high-resolution portion of our retinas (our foveolas) at the target.

A gimbal, under control of the image processing software that tracks the eye, moves the camera side to side (yaw/pan) and up and down (pitch/tilt). An exemplary gimbal for eye tracking was produced by LC Technologies, Inc. of Fairfax, Va. A focus motor drives the camera lens to keep the camera focused on the eye.

The eyefollower includes a mechanical configuration, control loop algorithms required to keep the camera pointed at and focused on the eye as the user moves his head, algorithms for rigorous trigonometric gazepoint tracking equations, called "explicit raytrace algorithms," for accurately predicting the user's gazepoint on the computer monitor, fully accommodating the variable camera geometry and the moving head, and an advanced "explicit calibration" procedure to accommodate the explicit raytrace algorithms. The eyefollower provides the desired head range of, for example, 18 inches side to side, ten inches forward and back, and eight inches up and down and tracks head velocities of 12 in/sec and accelerations of 30 in/sec/sec. Eyefollower-induced gazepoint tracking errors can be between 15% and 20% of the original gazepoint tracking errors achieved without the eyefollower. The eyefollower allows the present invention to be used by almost all people, including the majority of people with severe motor disabilities who have limited control of their head motion.

1. Exemplary Eyefollower Mechanical Design

The physical platform that manipulates the eyefollower camera is a motorized gimbal. The gimbal has a yaw (pan) and a pitch (tilt) axis to follow the user's left-right and up-down head motions. A motorized lens implements a variable-focus range to follow the user's forward-backward motions.

1.1 Direct Camera Pointing vs. Mirror Control

Mechanically, pointing the camera's view can be achieved either directly, by moving the camera, or indirectly, by placing a pivoting mirror in front of the lens. A rotatable mirror used to direct a camera's field of view is described, for example, in U.S. Pat. No. 5,090,797, which is incorporated by reference herein. The lower moment of inertia results in faster, smoother tracking performances.

Another embodiment of the present invention uses an approach of manipulating the camera directly. This approach eliminates the mirror component from the eyefollower assembly. Additionally, because of the mirror's reflection optics, the angular precision required for camera control is only half that required for mirror control.

1.2 Camera Pointing Mechanism

An exemplary camera pointing mechanism has been produced by LC Technologies, Inc. In this camera pointing mechanism, a pair of motors drives a camera platform to manipulate the camera's pointing direction. The yaw (pan) mechanism is shown in the top of the image, and the pitch (tilt) mechanism is shown on the bottom left.

1.3 Camera Focus Mechanism

An exemplary camera focusing mechanism has been produced by LC Technologies, Inc. In this camera focusing mechanism, a lens motor rotates the lens's focus ring to control the camera's focus range. One method for keeping the camera focused on the eye is described, for example, in U.S. Pat. No. 4,974,010 (hereinafter "the '010 patent"), which is incorporated herein by reference. An asymmetric aperture is used to unambiguously measure any out-of-focus condition on the eye's corneal surface, and that out-of-focus condition is used to drive the camera lens to restore focus on the eye.

1.4 Motors and Gears

Stepper motors are used to drive all axes in the eyefollower. Appropriate gear reductions are used to match optimum motor speeds with desired gimbal velocities.

1.5 Position Feedback Sensors

As mentioned earlier, a key advantage of the eyefollower is that its impact on the eyegaze system's overall gazepoint-tracking accuracy is minimal. Specifically, the goal is that the net gazepoint tracking errors resulting from gimbal-axis measurement errors be less than 20% of the gazepoint tracking errors resulting from the image processing errors.

Using explicit raytrace algorithms, the calculation of the user's gazepoint on the computer screen is directly dependent on the 3-D measurement of the eyeball's location and orientation in space. To obtain accurate eyeball location and orientation from a moving camera, it is required to know precisely where the camera is pointed and focused at all times.

High precision sensors are used to provide accurate position feedback on all eyefollower axes. The use of these sensors, as opposed to motor encoders, minimizes the effects of hysteresis (backlash) in the gear drive trains.

2. Exemplary Eyefollower Control

Control algorithms are required to achieve rapid, smooth, and stable operation of the eyefollower as it follows the user's eye. The control algorithms in the eyefollower fall into two categories. The first is camera direction control, i.e. keeping the camera pointed at the eye. The second is focus control, i.e. keeping the camera lens clearly focused on the eye.

2.1 Camera Direction Control

The eye image processing software naturally produces information about where the eye is within the camera's image. It is therefore straightforward to develop feedback control loops for the gimbal's yaw (pan) and pitch (tilt), to keep the camera pointed at the eye.

The objective of the gimbal's direction-control algorithm is to keep the center of the eyeball positioned in the center of the camera image. By keeping the camera aimed at the eyeball center, rather than either the glint spot or the pupil center alone, the gimbal moves only in response to lower-speed head motions, not in response to high-speed saccadic eyeball rotations within the head.

The data processing portion of the direction-control loop is based on the eyegaze system's eye image processing. As the head initiates movements side to side and up and down, the image of the eye initially moves within the video image. As the eye moves away from the center of the video image, velocity commands are issued to the yaw and pitch motors to restore the eye to the center of the screen. Thus the camera, through its generation of a video image, produces the optical feedback necessary to control the pitch and yaw motors.

2.2 Camera Focus Control 2.2.1 Alternative Range Measurement Approaches

It has often been suggested that ultrasonic, infrared, or optical range finders be used to measure the range to the eye. Given a range measurement, it would then be possible to control the lens. These approaches are not optimal for measuring the range to the eye, however, because they do not single out the cornea of the eye when they measure range. They can get ambiguous reflections from the forehead, nose, cheeks, or a person's glasses.

The present invention controls the focus condition of the eye by evaluating the clarity of the eye image itself. An image processing procedure measures the focus condition on line and produces a control signal for the lens motor to continually optimize the eye image focus.

2.2.2 Focus Direction Ambiguity

The magnitude of the eye's focus error can be easily estimated by evaluating the eye image blur. However, with conventional camera optics, there is no information within an out-of-focus image of an eye that indicates whether the camera is focused too near or too far. Thus, there is no information about what direction to turn the lens's focus ring in order to restore focus. Without knowing the polarity of the focus error, the development of an effective focus control loop is not possible. The crux of the lens control problem is knowing which way to turn the lens when it is out of focus.

An additional element of the focus-control problem is focus range measurement: for accurate gazepoint calculation, it is necessary to measure the range to the corneal surface of the eye with an accuracy of a few tenths of an inch. Thus, as the user moves his head, the eyefollower of the present invention knows what direction to adjust the lens focus ring, and is able to precisely measure the range to the corneal surface of the eye.

2.2.3 Asymmetric Aperture Method for Resolving Focus Direction Ambiguity

An "asymmetric aperture method" is used resolve the ambiguity of whether a camera is focused before or beyond a point source of light. An exemplary gaze tracking system and an exemplary asymmetric aperture method are described in the '010 patent. The asymmetric aperture method uses an asymmetric camera aperture to generate focus error polarity information. This information is available within the camera's image of the eye's corneal reflection. Software was written to measure the out-of-focus error using the asymmetric aperture method.

In an exemplary asymmetric camera lens aperture, a partial obstruction is placed in front of the camera lens to make the usually round lens aperture into an asymmetric shape. In an eyegaze system, the support bar that holds the LED in the center of the lens also acts as the optical obstruction.

In the eyegaze system, the corneal reflection from the LED appears to the camera as a point source of light. In an idealized optics system, as a point-source blurs out of focus, the near-field optics of the camera lens cause the image on the camera sensor to take the shape of the lens aperture. If the lens length is set too short, which corresponds to the camera being focused beyond the light source, the shape of the image on the camera sensor takes the same orientation as the aperture. If the lens length is set too long, which corresponds to the camera being focused before the source, the shape of the image takes an inverted orientation. Thus, the orientation of the image resolves the too-near/too-far ambiguity.

Also, in theory, the size of the image varies in direct proportion to the magnitude of the lens length error. Thus the point-source image, as measured from a single video frame, provides both the direction and magnitude information necessary to generate a corrective command to the focus motor.

Digitized video images of an eye taken at different ranges, while holding the focus range of the camera constant, clearly show that information regarding both the magnitude and direction of the out-of-focus range is contained in the image of the corneal reflection. In conformance with the theory, the magnitude of the image size, i.e., the blur, increases proportionately with the magnitude of the out-of-focus range, and the polarity of the direction is contained in the orientation of the shape.

2.2.4 Size of the Corneal Reflection

In another embodiment of the present invention, the size of the corneal reflection is measured. The size of the corneal reflection is, for example, the blur magnitude of the corneal reflection size. The size of the corneal reflection is measured, for example, by its pixel dimensions within the video image. The raw dimensions of the corneal reflection are determined by calculating the 2-dimensional standard deviation of the intensity distribution.

Though the size of the corneal reflection varies predominantly in proportion to the lens length error, there are additional complicating factors. Even if the corneal reflection is in perfect focus, its dimensions do not reduce to zero as predicted by the theory. There can be some image spread due to, for example, a) a finite size of the real LED light source, b) the quantization of the camera pixel grid, and c) bleeding within the camera sensor electronics. Secondly, if there is side-to-side or up-and-down motion of the eye within the image, the size of the image can increase due to smearing resulting from the camera aperture being open for a finite period of time, independent of the lens being out of focus.

From an optics point of view, the total intensity distribution of the corneal reflection image is the optical convolution of a well-focused, stationary corneal reflection, the profile of an impulse in motion on the camera sensor, and the shape of the camera aperture cast on the camera sensor, which varies in magnitude as the corneal reflection goes out of focus.

The variance of a convolved signal is equal to the sum of the variances of the constituent parts. Thus the total measured variance of the corneal reflection image is the sum of a) the variance of a nominal well-focused, still corneal reflection, b) the variance of the profile of an impulse in motion on the camera sensor, and c) the variance due to the image being out of focus, i.e., the variance of the camera aperture's image on the sensor. The variance due to the image being out of focus is solved by subtracting the nominal and velocity variances from the total measured variance.

2.2.5 Orientation of the Corneal Reflection

An algorithm for computing the orientation of the corneal reflection image can be based on knowledge of the shape of the aperture. The aperture shape on an eyegaze system camera consists of a circular disk with a bar protruding from one side. To determine the orientation of the image, the algorithm examines variations between the right and left sides of the isolated corneal reflection image. One possible approach is look for the "shadow" of the LED support bar. The shadow would appear as a dip in the center of an intensity profile taken vertically through the side of the corneal reflection image. Another approach is to compute moment generating functions for the distributions on each side. The side with the shadow should contain relatively higher second and fourth order moments. As mentioned above in discussing focus measurement tests, the quadratic curvature measure can be effective in assessing the orientation of the corneal reflection, and it can have the added benefit that magnitude of the curvature varied fairly linearly with the true focus error, making it an effective feedback signal for lens focus control.

2.2.7 Focus Control Loop

In an exemplary feedback control loop for controlling a video camera lens, a video camera continually generates video images of the user's eye, and the frame grabber digitizes the images for processing by the focus analysis functions. The eyegaze system's pattern recognition software then detects and isolates the corneal-reflection image. The focus analysis functions measure the quadratic curvature in the corneal reflection and compute the present lens-length error. The control logic generates lens motor commands based on the lens-length error.

Stable closed-loop operation of the focus control loop is achieved using a proportional control algorithm to generate velocity commands for the lens motor. A motor interface board in the computer converts the software velocity commands to motor voltages that drive the lens control motor. As the user moves his head back and forth, the focus control loop continually adjusts the lens to keep the eye in clear focus.

2.3 Outer and Inner Control Loops

The eyefollower's overall control structure can consist of an outer command loop and an inner control loop.

2.3.1 Outer Command Loop

As discussed above, the outer command loop obtains eyeball position information from the camera images, and generates velocity commands for the eyefollower's pitch, yaw, and focus motors. Because the outer command loop obtains its feedback information from the camera images, it is restricted to operate at a camera frame rate of, for example, 60 Hz.

2.3.2 Inner Control Loop

The inner control loop receives the velocity commands from the outer command loop and generates smooth, high-speed position profiles for the eyefollower motors to follow. Precision motor controllers (i.e., National Semiconductor LM-629's) are used to provide the eyefollower motors with continuous control during the 16.7 ms periods between the 60 Hz command updates. The controller chips generate smooth inner-loop set-point profiles in response to the step commands provided by the outer loop each camera period, and provide continuous, stable, high-speed feedback control.

The profile generators have programmable position, velocity, and acceleration limits. The high-speed controllers use motor encoders to provide high-speed real-time position feedback. Motor position commands to the controller chips are defined in terms of motor counts, so the eyefollower control software in the host computer converts gimbal angle commands from radians to motor counts and converts lens-length commands from millimeters to motor counts.

For outer-loop feedback control purposes, the host computer software samples the gimbal and lens motor positions at the end of each camera field period. The software converts the sampled gimbal motor counts to radians, and converts the lens motor counts to millimeters.

3. Exemplary Gazepoint Calculation

The ultimate objective of the eyetracking instrument, of course, is to compute the coordinates of the user's gazepoint on the computer screen. Given that the eyefollower is now properly tracking the eyeball as the user is moving his head around, the next task is to accommodate the variable camera geometry in the gazepoint calculation. The procedure used for accommodating variable camera geometry in the gazepoint calculation is called the "explicit raytrace algorithm."

There are many circumstances where it is desired to know what a person is looking at. In visual attention tasks, for example, it is desirable to know whether is person is visually attending to his task. In teaching a child to read, it is desirable to see how his gaze tracks through text. People with severe motor disabilities can communicate and operate computers simply by looking at control buttons displayed on a screen.

Since there is no physical manifestation of a gazepoint that can be measured directly, eyetracking systems measure the gazepoint indirectly by observing the eye with a camera and calculating where the eye's line of sight intersects the scene being viewed.

The distribution of rods and cones over the retinal surface of human eye varies significantly. In particular, there is an extremely dense concentration of cones within what is called the macular region, and the highest density of cones occurs within the foveola at the center of the macular region. The foveola has a radius of approximately 0.6 degrees. When a person fixes his gaze on an object of interest, he points his eyes such that the light from that object lands on the foveola, providing the eye with a very high-resolution image of that object.

Because humans point their eyes precisely at objects they wish to view, and because the eyes are visible from outside the body, it is feasible to infer what people are looking at by observing their eyes. In the field of video eyetracking, video cameras are typically used to monitor the eyes, measure their orientations, and predict where they are looking.

Physically, the gazepoint is defined as the 3-dimensional point in space where the eye's visual axis intercepts the object being observed. The eye's visual axis, also known as the gaze axis, gaze line sight line, or line of sight, is the optical path of the central, straight-line ray that passes from the center of the foveola, passes through the eye's two optical nodal points, and ultimately terminates at the gazepoint. Thus, in another embodiment of the present invention, the gazepoint is computed by projecting the gaze line from the eye's location in space to the point where the line intercepts a visible object.

3.1 Lumped-Parameter Raytrace Algorithms

Historically, many image-processing methods have been developed to measure the eye's orientation from information within a camera's image of the eye. Eyetracking methods can include measuring the locations of the pupil, the iris, and/or light reflections off any number of reflective surfaces on and in the eye (including both the anterior and posterior surfaces of both the cornea and the lens) as the eye rotates. One method for measuring eye orientation is called the pupil-center cornea-center (PCCR) method, wherein the eye is illuminated by one or more light sources and the eye's orientation is measured as a function of the relative location of the pupil center with respect to the corneal reflection(s).

For purposes of determining where a person is looking, it is generally necessary to know more about the eye than just its orientation. It is also necessary to know about the scene that the person is observing, and about where the eyeball is located (as well as oriented) with respect to the scene. The rigorous calculation of the gazepoint involves a) measuring the 3-D location of the eye in space, b) measuring the angular orientation of the eye, c) computing the gaze line from the eye location and orientation, and d) projecting the gaze line until it intercepts a visible object in the scene.

One application of video eyetracking, however, involves the calculation of a person's gazepoint on a viewing surface such as a video screen or computer monitor. In this case, the scene may be defined as a 2-dimensional space, and the gazepoint may be calculated as the 2-D point where the 3-D gaze line intercepts the 2-D surface. In this special case of measuring a gazepoint on 2-D surface, it is not necessary to explicitly measure the eyeball location in order to estimate the gazepoint. Given that a) a person is viewing a 2-D surface such as a computer monitor, b) the camera is fixed with respect to the scene, and c) the head does not move significantly, it is possible to approximate the 2-D gazepoint on the screen based on simple equations that depend only on position measurements of the pupil and/or corneal reflections within the camera image. In this case, the complex non-linear geometry of measuring the eye location in 3-D space, measuring the eye orientation, calculating the gaze-line, and computing the gaze-line intersection with the display surface may be reduced to a set of simple, linear equations that approximate the gazepoint fairly accurately over limited ranges of head position and gaze angles.

In its simplest form, the PCCR equations, for example, reduce to $$X_{gaze}=A_0+A_i*d_i \text{ (mm)} \quad (1)$$

$$Y_{gaze}=B_0+B_j*d_j \text{ (mm)} \quad (2)$$

where i an j are the horizontal and vertical pixel coordinates of the pupil and corneal-reflection images within the camera image, di and dj represent the glint-pupil vector (taken from the classic Pupil-Center/Corneal Reflection [PCCR] method):

$$di=i_{pupil}-i_{glint} \quad (3)$$

$$dj=j_{pupil}-j_{glint} \quad (4)$$

and $\{A_0\ A_i\ B_0\ B_j\}$ is a set of "calibration constants."

In these equations, the parameters $A_0$, $A_1$, $B_0$, and $B_1$ collectively account for a variety of physical effects, including eyeball anatomy parameters, distance from the camera to the eye, camera angle, camera lens parameters, and camera sensor parameters. Because the few parameters in these equations simultaneously represent multiple physical phenomena, the equations are referred to as "lumped parameter" models. The constant terms $A_0$, $A_i$, $B_0$, $B_j$ correspond to first-order gain and offset terms for approximating the gazepoint as a function of the glint-pupil vector.

A key advantage of these simplified, lumped-parameter models is that appropriate parameter values may be computed by eyetracking calibration procedures. In these eyetracking calibration procedures, the user visually follows a dot around to different locations on the display, and regression algorithms are used to compute "optimum" parameter values that yield the best gazepoint predictions over the calibrated data ranges.

The linear terms $A_i$ and $B_j$ account for the variable horizontal and vertical rotations of the eye. For gaze angles within about 15 degrees of the camera, variations in the gazepoint vary approximately linearly with the glint-pupil vector di,dj. For larger gaze angles from the camera, the linear approximations become appreciably worse.

More sophisticated lumped parameter models may, of course, be developed to better accommodate known nonlinearities and to permit wider ranges of relatively accurate gazepoint tracking. Significant nonlinearities are introduced by the screen being significantly tilted with respect to the camera Z axis, the corneal surface of the eye flattening out toward the edges, computer screen curvature, and the camera roll angle not being perfectly aligned with the monitor, which introduces cross coupling between the x-y components of the glint-pupil-vector and the x-y components of the gazepoint.

To partially accommodate some of the known nonlinearities, the above Equations 1 and 2 may be expanded to:

$$X_{gaze}=A_0+A_i*di+A_j*dj+A_{ij}*di*dj \text{ (mm)} \quad (1a)$$

$$Y_{gaze}=B_0+B_i*di+B_j*dj+B_{jj}*dj^2 \text{ (mm)} \quad (2a)$$

The "cross" terms $A_j*d_j$ in $x_{gaze}$ and $B_i*di$ in $y_{gaze}$ allow for roll angle misalignment between the camera's and monitor's horizontal axes. Thus, purely horizontal eye motion in the camera image may yield some vertical variation in the calculated gazepoint and vice versa.

The $A_{ij}*di*dj$ term in $x_{gaze}$ and the $B_{jj}*dj^2$ term in $y_{gaze}$ amount to scale factors on di and dj such that the gains of di on $x_{gaze}$ and dj on $y_{gaze}$ vary as a function of how high (dj) on the screen the user is looking. Within the range of the computer screen, these two nonlinear terms accommodate most of the nonlinearity associated with the tilt of the screen. The $B_{jj}*dj^2$ term in $Y_{gaze}$ also accommodates corneal flattening.

3.2 Exemplary Explicit Raytrace Algorithms of the Present Invention 3.2.1 Introduction With the addition of the eyefollower (including its pitch/yaw gimbal and autofocus mechanism) to the eyegaze system, the lumped parameter Equations 1a and 2a become inadequate for accurate gazepoint calculation. Even with a fixed camera configuration, Equations 1 and 2 only approximate the full geometry of the optics and mechanics of the true gaze optics and measurement equipment. With the variable geometry of the eyefollower, these lumped parameter equations are rendered far more inadequate, leading to significant gazepoint tracking errors as the gimbal pitch, yaw and focus range vary over any significant ranges. With the eyefollower, more sophisticated models of the gaze-line optics and measurement equipment are required to compute the gazepoint accurately.

An embodiment of the present invention is a method that explicitly accounts for variations in head position, camera pointing angle, and camera focus range. This section describes exemplary rigorous, "explicit" raytrace methods of the present invention that trace optical rays, accommodate gimbal and lens movements, and compute full trigonometric transformations.

Given an eyetracker with a gimbal, accurate measurement of the gazepoint must correctly account for the following optical phenomenon and physical implementation of the equipment. (Recall: since there is no physical manifestation of a gazepoint that can be measured directly, eyetracking systems compute the gazepoint indirectly by observing the eye with a camera, modeling the eye's and camera's optics, and modeling the equipment geometry. In this case, the equipment includes a moving camera on a gimbal.)

1. Gazepoint

A user views a scene within a space defined here as the "world" coordinate frame. When the user looks at an object within the world frame, the 3-D point of his gaze on that object is referred to as the gazepoint or point of regard.

2. Eyeball Location and Orientation

A user views the scene from the point of view of his eyes. Ideally, the user is free to move his head, so the locations of the eyes move freely within the world frame. (Note: the discussion here addresses gazepoint computation for a single eye. If a "binocular" eyetracker tracks both eyes, this computational process may be duplicated for both eyes.)

3. Gaze Line

When a user looks at an object within the world frame, his eye's visual axis is pointed toward the object. Thus the user's gaze axis, also known as the gaze line, is a line in the world coordinate frame that passes through two points: the eye and the object being observed. For gazepoint-calculation purposes, it is necessary to define a specific reference point within the eye to be the origin of the eye's coordinate frame. Alternative reference locations for the eye include: the center of the foveola on the retina, the center of the eyeball sphere, one of the eye's two optical nodal points (located close to the center of the corneal sphere), the pupil center, and the center of the corneal surface. For simplicity purposes in calculating the gaze point, it is desirable that the eye's origin be defined to lie on the eye's gaze line. In the preferred embodiment of this invention, the eye's origin is taken to be the first nodal point.

4. Camera

To obtain information on where the eye is located and how it is oriented in space, an eyetracker views the user's eye with a camera. Image-processing algorithms analyze the eye image to determine the location and orientation of the eye within the camera coordinate frame. A wide range of well known image processing algorithms exist in the video eye-tracking field to measure the eye's location and direction.

5. Gimbal

A gimbal mechanism keeps the camera pointed at the eye, and the autofocus mechanism keeps the camera lens focused on the eye. As the eyefollower rotates and re-focuses, the relative location and orientation of the eye, as the image processing originally computed within the camera frame of reference, change with respect to the gimbal-base frame. (Note: Though the objective of the gimbal control is to keep the camera generally pointed at and focused on the eye, it is not necessary for accurate gazepoint calculation that these control loops operate error free. As long as the gimbal keeps the eye image somewhere within the camera field of view, the image processing can measure the image and compute the eye's location precisely within the camera frame.)

6. Gimbal Location in World Frame

The "base" of the gimbal platform is typically (though not necessarily) located at a fixed position and orientation within the world coordinate frame. Given that the location and orientation of the gimbal-base frame is known within the world frame, it is finally possible to achieve the eyetracker's original objective of computing the user's gazepoint within the world frame.

Based on the physical configuration of the above described scene/eye/camera/gimbal/world system, an objective of computing a user's gazepoint within the scene involves transforming the user's gaze-line and gazepoint through a sequence of different coordinate frames. Coordinate transformations are the mathematical tools generally used to describe the relative positions and orientations of objects. Generally, a Cartesian coordinate frame may be defined for any object. Typically, an orthogonal set of "body" axes x, y and z is assigned to an object to define its various directions, and some fixed reference point (in, on or outside the object) is defined as the object origin x=0, y=0, z=0.

Once coordinate frames are defined for any two objects, the mathematics of coordinate-frame transformations may be used to compute the relative positions and orientations of the two objects with respect to each other [Richard Paul]. A transformation between any two coordinate frames is typically defined by six parameters, including three translational parameters $x_0$, $y_0$ and $z_0$ that specify the location of the origin of one frame with respect to the origin of the other, and three rotational parameters $\theta$, $\psi$ and $\phi$ that specify the angular orientation of one frame with respect to the other. Given these six parameters, any point, line, plane, or vector in one coordinate frame may be exactly calculated from the point, line, plane, or vector in the other frame.

One key characteristic of coordinate transform theory is that it accurately models the complex and highly nonlinear geometry of 3-dimensional object rotation. The earliest, fully-rigorous representation of 3-D object rotation was described by the 18$^{th}$ century mathematician Leonhard Euler. Euler showed that any angular orientation of an object within a Cartesian coordinate frame may be expressed exactly by a defined sequence of three rotations about successive body axes. (Assuming that the object begins in an orientation fully aligned with a given frame, the object may be rotated to any arbitrary 3-D orientation by a sequence of 3 rotations, first $\theta$ about any one of the 3 body axes, second $\psi$ about any body axis other than the first, and third $\phi$ about any body axis other than the second.)

In modern mathematics, the Euler angle transform is generally represented mathematically by a 3×3 matrix whose 9 elements are complex functions involving the sines and cosines of the angles $\theta$, $\psi$ and $\phi$. The elegance of the matrix approach is that a point, line, plane, or vector in one frame can be computed from the point, line, plane or vector in the other frame by simple matrix multiplication, and all the complex, nonlinear trigonometry of the rotational geometry is rigorously and exactly accommodated.

Coordinate transforms are particularly useful in describing objects that are in motion with respect to each other, where the motion includes both translation and rotation. The field of robotics, for example, makes extensive use of coordinate transform theory to monitor and control the motion of articulated arms. As joints rotate and links move, sensors continuously measure variations in the 6 fundamental parameters ($x_0$, $y_0$, $z_0$, $\theta$, $\psi$ and $\phi$) that relate each connected link; the coordinate transform for each connected link is computed from these parameters; the position and orientation of each successive link is computed with respect to its supporting link; and when all is said and done, the final position and orientation of the proverbial "finger tip" is precisely positioned to touch the target.

In the present invention, coordinate transforms are used in the eye-tracking application in a manner analogous to robotics. In this eye-tracking case, the links are not all mechanical. The gaze line between the eye and the gaze point, for example, is a figurative link that has no physical manifestation. For coordinate transformation purposes, however, the gaze line may be accurately represented mathematically as a link whose origin lies at the eye and whose direction is "connected" to the eye's orientation. The eyeball may be represented mathematically as an articulated "joint" that connects to the gaze-line "link." As the ocular muscles drive the eyeball to rotate in its socket, the attached gaze-line link swings around in space, allowing the eye to fixate on a target of interest to the user.

In the eye tracking application, the gaze line is the final link in the overall sequence of articulated links (analogous to the finger at the end of the robotic arm). The link preceding the eye-to-gazepoint link is the camera-to-eye link. It, like the gaze line, is optical, not mechanical. The length of the camera-to-eye link is the distance between the camera and the eye. The joint from the camera to the eye is also optical, not mechanical, but it is fully modelable by a coordinate transform. Let the camera z axis be defined to lie along the camera's optical axis, the x axis points to the camera's right and the z axis points out the camera's top. Let the origin of the camera frame of reference be the center of the camera sensor. The joint that connects the camera to the eye may then be defined as follows: the pitch angle $\theta$ is the vertical angle of the eye in the camera z-y plane; the yaw angle $\psi$ is the horizontal angle of the eye in the camera z-x plane; and the roll $\phi$ is the roll rotation of the eye with respect to the camera.

The joint preceding the camera-to-eye link is the gimbal mechanism that rotates the camera. This joint is mechanical, fully similar to a robot joint. In one embodiment of this invention, the gimbal joint consists of only two adjustable angles: a pitch angle $\theta$ and a yaw angle $\psi$. Given no adjustable camera roll angle, the angle $\phi$ may be defined to be a constant 0.

In the eyetracking application, the ultimate objective is to measure the user's gaze point within the world coordinate frame. Thus, the initial link in the overall sequence of eye-tracking coordinate transforms is the link that connects the gimbal-base frame back to the world coordinate frame.

Within the context of 3-D coordinate transforms, the world coordinate frame is generally a 3-D frame. The gaze point within a 3-D scene is generally defined as the point where the gaze line intercepts a visible object. In order to compute the 3-D gaze point, it is necessary to know the 3-D surface contours of the visible objects in the scene. In the future, it may become more feasible to measure such 3-D surfaces from real or simulated 3-D scenes, but with today's technology, such contours are typically not known, so it is generally not feasible to measure 3-D gaze points from a single eye.

As is well known in the eyetracking field, an alternative method for measuring a 3-D gaze point is to measure the gaze lines from both the user's eyes and compute the intersection of the two gaze lines. The underlying assumption is that the user's two eyes are pointed at the same object.

In one eyetracking application, the objective is to determine a user's gaze point on a 2-dimensional screen, such as a computer monitor. In this case, the user's gaze point may be easily computed as the intersection of the eye's gaze line with the 2-dimensional screen surface. The eyefollower camera emulates the human eye: the eyefollower rotates and refocuses its "eye," the camera, to follow its object of interest, the user's eye, around in space.

Once the image processing algorithms determine the location and orientation of the eye within the camera coordinate frame, the eye's location and orientation vector are rigorously transformed to the monitor coordinate frame. Given the eye's location and orientation within the monitor frame, it is then straightforward to project where the eye's gaze line intercepts the monitor screen surface.

In summary, the explicit raytrace algorithms compute the user's gazepoint by measuring the eyeball's 3-D location and orientation with the camera frame of reference, computing the gaze line of the eye within the camera frame of reference based on the eye location and orientation, converting the gaze line from the camera frame to the monitor frame, and projecting the gaze line from the eye to its intercept on the screen.

3.2.2 2-D Eyeball Position in the Camera Image

Recall that for the purpose of pointing the camera at the eye, it is desirable to point the camera at the center of the eyeball, not necessarily at the corneal reflection, the pupil center, or the center of the corneal sphere. Thus, the camera moves in response to overall head motions, not in response to rapidly moving eyeball saccades rotations.

Calculating the eyeball's 3-D location in the gimbal base frame begins with the computation of the eyeball's 2-D position within the camera image. FIG. 1 is a schematic diagram 100 showing a location of an eyeball center with respect to a pupil center and corneal reflection. As illustrated in FIG. 1, the center of the eyeball lies (approximately) on the eye's optic axis at a fixed distance $D_{eb\text{-}cs}$ behind the center of the corneal sphere. Recall that the pupil center also lies on the optic axis, at a distance Rho in front of the center of the corneal sphere. Since the eyeball center is co-linear with the center of the corneal sphere and the pupil center, the eyeball center location ($x_{eb\_img}$, $y_{eb\_img}$) within the camera image is a simple linear combination of the glint and pupil locations:

$$x_{eb\_img} \sim = x_{cr\_img} - K_{eyeball} * (x_{cr\_img} - x_{pc\_img}) \text{ (camera image)} \quad (5)$$

$$Y_{eb\_img} \sim = y_{cr\_img} - K_{eyeball} * (X_{cr\_img} - y_{pc\_img}) \quad (6)$$

where the eyeball constant $K_{eyeball}$ is the ratio $$K_{eyeball} = D_{eb\text{-}cs}/Rho \quad (7)$$

Because it is unrealistic to measure $D_{eb\text{-}cs}$ for individual eyes, $K_{eyeball}$ in the eyegaze system is taken to be a constant for all people.

3.2.3 3-D Eyeball Position in the Camera Frame of Reference

The full 3-D location of the eyeball center within the camera frame is computed as a function of the eyeball position within the camera image, and the range from the camera sensor to the virtual corneal reflection point.

The range $z_{eyeball}$ from the camera sensor to the virtual corneal reflection point is given by the sum of the true camera focus range $R_{foc}$, the focus range offset $R_{foc\_off}$, and the distance between centers of the eyeball and corneal spheres $D_{eb-cs}$:

$$z_{eyeball} = R_{foc} + R_{foc\_off} + D_{eb-cs} \text{ (camera frame)} \quad (8)$$

The camera focus range $R_{foc}$ is computed by measuring the current camera lens length L (as controlled by the focus control loop discussed in Section 0) and solving the Gaussian lens equation:

$$1/R_{foc} + 1/L = 1/F \quad (9)$$

where F is the lens focal length.

The eye image processing functions in the eyegaze system produce the focus range offset $R_{foc\_off}$ between the camera focus plane and the corneal reflection point. Now knowing the range $z_{eyeball}$ from the camera sensor to the eye, the distance $D_{lens\_eye}$ from the lens to eye is found by subtracting the lens length $L_{lens}$:

$$D_{lens\_eyeball} = z_{eyeball} - L_{lens} \quad (9)$$

Finally, the x and y components of the eye location are computed by triangulation through the camera lens:

$$x_{eyeball} = x_{eb\_img}(D_{lens\_eyeball}/L_{lens}) \text{ (camera coordinate frame)} \quad (10)$$

$$y_{eyeball} = y_{eb\_img}(D_{lens\_eyeball}/L_{lens}) \quad (11)$$

3.2.4 3-D Eye Location and Orientation within the Camera Coordinate Frame

For purposes of calculating the 3-D gaze line within the camera frame of reference, it is necessary to compute the 3-D location and orientation of the eye within the 3-D camera frame. The eye's 3-D location and orientation are derived from the 2-D camera image of the eye and the knowledge of the range from the camera to the eye, as measured, for example by the asymmetric aperture method. When using optical methods, such as an illuminator and a camera, to measure an object, it is clearly important to account properly for the optical properties of both the measurement equipment and the object. Camera optics, well known in the art, are not discussed here. Toward the objective of obtaining improved accuracy in the measurement of an eye's location and orientation, the optics of the eye are discussed.

When measuring the precise location and orientation of an eye from a camera image, it is necessary to know several anatomical characteristics of the eye. In particular, it is necessary to know a) the orientation of the visual axis within the eye and b) the precise shape of the visible surfaces of the eye.

The general shape of the human eye is well known. For example, the foveola is known to lie to the temporal side of the retina, resulting in an angular difference between the eye's optical and visual axes. In the eye's horizontal plane this angle Kappa, $K_{horz}$, is generally about 4±1 degrees, and in the eye's vertical plane $K_{vert}$ is approximately 0±1 degrees. The direction of $K_{horz}$ is typically opposite for the left and right eyes.

The corneal surface is known to be generally spherical at the center, to flatten slightly toward the edges, and to possess some astigmatism. Though the cornea is often modeled as a simple sphere, the flattening and astigmatism properties shift the location of the corneal reflection with respect to the spherical model, particularly when the eye is oriented at large angles away from the camera. Thus, flattening and astigmatism must be accommodated explicitly to measure the eye's location and orientation accurately.

The general shape of the cornea may be better modeled as an elongated ellipsoid. In one representation, the ellipsoid has a nominal radius of curvature $R_{nom}$ at the center of the cornea, an elongation coefficient $E_{elong}$ defining the flattening of the corneal curvature toward the edges, an astigmatism parameter $\rho_{astig}$ defining the degree of astigmatism on the corneal surface, and a parameter $\theta_{astig}$ defining the angle of astigmatism on the corneal surface.

The specific characteristics of individual eyes, of course, vary over the general population of human eyes. To measure a gaze line with an accuracy of better than about three or four degrees, it is generally necessary to know specific parameter values for the given eyes, rather than to use typical values. Thus, for example, when modeling the eye as described above, it is desired to have specific values for $K_{horz}$, $K_{vert}$, $R_{nom}$, $E_{elong}$, $\rho_{astig}$, and $\theta_{astig}$. At this point in the discussion, let us assume that the eye's anatomical feature set is known. (See the later discussion on calibration for a procedure to infer these anatomical eye parameters for a given eye.)

By the laws of optics, the corneal reflection occurs at the point on the corneal surface where the incident angle of the light from the eyetracker's illumination source reflects off the cornea at the same angle as the reflected ray to the center of the camera aperture. To simplify the discussion here, let us take the case where the eyetracker's illumination is located at the center of the lens. In this case, the corneal reflection occurs at the point on the corneal surface that is normal to the illuminator. Note: this simplification is not required for exact ray tracing.

In the pupil-center-corneal-reflection method, the orientation of the eye within the camera frame is computed as a function of the vector distance $(x_{gpv}, y_{gpv})$ from the corneal reflection to the pupil center. (The corneal reflection is often referred to as the glint, and the subscript gpv stands for glint-pupil vector.) If the eye's optic axis is oriented directly toward the camera, the corneal reflection is located at the center of the pupil, and the magnitude of the glint-pupil vector is zero. As the eye's optic axis rotates away from the camera, the magnitude of the glint pupil vector increases. The magnitude m of the glint-pupil vector is directly related to the eye's angle $\alpha$ away from the camera axis, and the direction of the vector within the camera image indicates the angle $\beta$ with respect to up/down/right/left. Given a simplified spherical model of the corneal surface (with a radius $R_{nom}$), the projection of the corneal reflection ray (from the camera illuminator at the center of the lens to the reflection point on the corneal surface) always passes directly through the center of the corneal sphere. In this case, the angle $\alpha$ may be computed as:

$$\alpha = \sin^{-1}(m/R_{nom})$$

and the angle $\beta$ may be computed as:

$$\beta = a\tan 2(y_{gpv}, x_{gpv})$$

Given a more general ellipsoidal model of the corneal surface, however, the projection of the corneal reflection ray does not generally pass through the center of the corneal sphere. With corneal flattening and astigmatism, the reflective optics governing the location of the corneal reflection on the corneal surface itself become significantly more complex to model mathematically, making the angles $\alpha$ and $\beta$ more difficult to compute. Without the spherical assumption, the equations for the location of the corneal reflection become implicit and cannot be solved directly.

Typically, iterative approaches must be used to solve implicit equations. Following is an iterative approach for finding the eye position $(y_{gpv}, x_{gpv})$ and the eye angles $(\alpha, \beta)$ within the camera's 3-D frame of reference.

Figure 2:
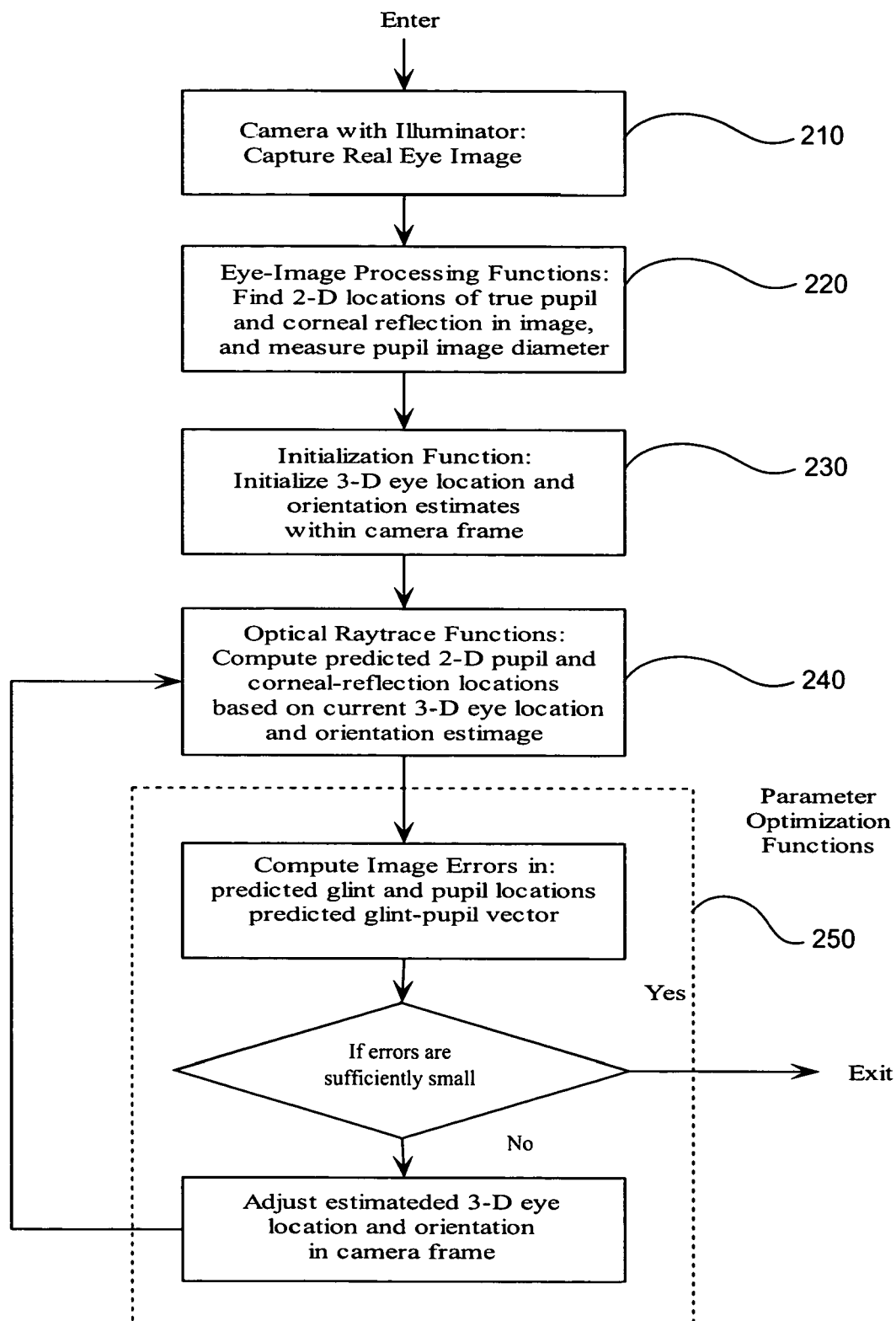
FIG. 2 is a flowchart showing a method for computing a position and orientation of an eye within a camera's coordinate system, in accordance with an embodiment of the present invention.

FIG. 2 is a flowchart showing a method 200 for computing a position and orientation of an eye within a camera's coordinate system, in accordance with an embodiment of the present invention.

In step 210 of method 200, a camera captures a real image of the eye. An illuminator is used with the camera to generate a corneal reflection off the eye.

In step 220, image processing functions analyze the camera's image of the eye to find the 2-D locations of the true pupil center and corneal reflection within the camera image, and to measure the diameter of the pupil image. Additionally, a range analysis is performed, using the asymmetric aperture method for example, to compute the range $z_{eye}$ from the camera to the eye.

In step 230, the eye is initially assumed to exist at some horizontal and vertical location ($x_{eye}$, $y_{eye}$) and to have an orientation ($\alpha$, $\beta$) within the camera frame of reference. Note: Good initial estimates of $x_{eye}$, $y_{eye}$, $\alpha$, and $\beta$ are generally not required to obtain a final solution, but do reduce the computational load required to reach the solution. Good initial estimates may be computed using a spherical model of the eye.

In step 240, given the current 3-D estimate of the eye location and orientation within the camera frame of reference, optical ray-tracing functions are used to compute predicted 2-D locations of the pupil center and corneal reflections within the camera image that would occur if the eye were at its estimated location and orientation. These optical ray-tracing functions model the illuminator, the eye shape, and the camera, and they provide the precision required for accurate optics measurement of the eye's position and orientation.

In the preferred embodiment of this invention, the shape of the corneal surface is defined as an ellipsoid with a nominal radius $R_{nom}$ at the center of the cornea, an elongation coefficient $E_{elong}$ that defines the flattening of the corneal curvature toward the edges, an astigmatism-magnitude parameter $\rho_{astig}$ defining the degree of astigmatism on the corneal surface, and an astigmatism-angle parameter and $\theta_{astig}$ defining the angle of astigmatism on the corneal surface. Given this ellipsoidal model of the corneal surface topography, and given an estimated location and orientation of the eye within the camera frame of reference, the location of the corneal reflection within the camera image may be computed precisely by rigorous application of the law of reflection. Because of the complex mathematics involved in finding the reflection point on a complex surface, iterative ray-tracing procedures are typically used to calculate the corneal-reflection point.

Also, in the preferred embodiment of this invention, the optical ray-tracing functions account for the refraction of the pupil image that results from the camera viewing the pupil through the curved corneal surface. For purposes of measuring the eye orientation, the pupil center is taken to be a fixed reference point on the eye. The pupil, however, lies a couple millimeters behind the corneal surface. Further, the pupil center is not directly observable. Generally, its location is inferred indirectly by detecting the visible pupil perimeter and then calculating the center point from the observed perimeter. As the pupil dilates and constricts, and as the eye's orientation changes with respect to the camera, the curved surface of the cornea refracts the different points on the pupil perimeter differently. Thus, an apparent pupil center, computed as the simple center of the perimeter points, does not accurately represent the true location of the pupil center. By properly modeling the pupil image refraction, however, the true pupil center may be computed more precisely, resulting in more accurate gazepoint calculation. Precise calculation of the true pupil-center location from the pupil-center image, of course, requires knowledge of the corneal surface topography and the application of the optical law of refraction (Snell's law). In the preferred embodiment of this invention, the corneal surface is modeled as the previously described ellipsoid, and the optical rays from the edge of the pupil to the camera lens are calculated to refract at the corneal surface. (The refractive index of the cornea, 1.37, is highly consistent over the human population, so the value need not be estimated for each individual eye.)

In step 250, parameter optimization functions compare the true and predicted glint and pupil locations, and the errors between the true and predicted values are used to adjust the estimated eye location and orientation. In particular, the vertical and horizontal errors in the predicted glint location within the image are used respectively to adjust the estimated eye locations $x_{eye}$, $y_{eye}$ within the camera frame, and the vertical and horizontal errors in the predicted glint-pupil vector are used to adjust the eye orientation $\alpha$, $\beta$.

Steps 240 and 250 are iterated until the predicted and true glint and pupil locations in the camera image match with a desired accuracy.

3.2.5 Coordinate Systems

Figure 3:
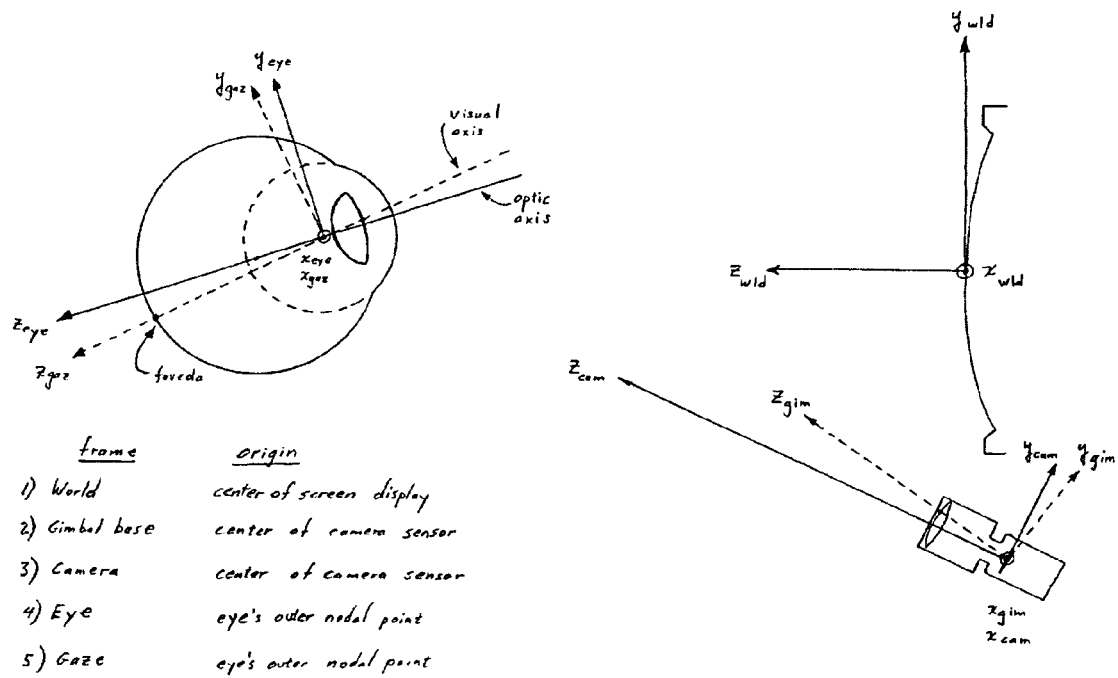
FIG. 3 is a schematic diagram showing coordinate frames for explicit raytracing, in accordance with an embodiment of the present invention.

FIG. 3 is a schematic diagram 300 showing coordinate frames for explicit raytracing, in accordance with an embodiment of the present invention. As illustrated in FIG. 3, five reference coordinate frames are defined for explicit ray tracing in the eyegaze system with the eyefollower. The fundamental units of position measurement in all coordinate frames are millimeters, and the units of angle measurement are radians. All coordinate frames are right-handed x-y-z frames.

1. World (Monitor) Frame

When tracking the gazepoint on a computer monitor screen, the world coordinate frame is defined with respect to the monitor screen. In the eyegaze system, the origin of the monitor frame is defined to be center of the computer monitor screen's display area. The x axis is positive to the user's right, the y axis is positive upward, and the z axis is positive out of the screen.

Gazepoint coordinates must be computed, of course, in the monitor frame. Thus the coordinate ($x_{gaze}$, $y_{gaze}$) is defined to be (0,0) at the center of the screen, $x_{gaze}$ is positive to the right, and $y_{gaze}$ is positive upward.

2. Gimbal-Base Frame

Commonly referred to simply as the "gimbal" frame, the gimbal-base frame is defined to coincide with the camera frame when the gimbal pitch and yaw angles are both at their nominal zero values.

3. Camera Frame

The origin of the camera frame is defined to be the center of the camera sensor chip, which is fixed within the camera body. The x axis is positive to the right for an observer looking into the camera lens, y is positive upward, and z is positive out the camera lens. All image measurements are made in the camera frame of reference.

4. Eye Frame

The origin of the eye frame is defined to be located at the eye's outer nodal point, i.e., the center of the cornea curvature. The eye's z axis is coincident with the optic axis of the eye, but points positively through the back of the eye. Given that the eye is horizontally oriented (i.e. its roll angle is zero), the y axis is positive upward and the x axis is positive to the eye's right.

The eye frame, which represents the physically observable eyeball, is key because the camera observes and measures the orientation and location of the physical eye, with respect to the camera frame of reference.

5. Gaze Frame

As in the eye frame, the origin of the gaze frame is defined to be the eye's outer nodal point, so it is coincident with the origin of the eye frame. The z axis of the gaze frame, however, is defined to pass through the center of the foveola, and thus the minus z axis is coincident with the eye's visual axis, not its optic axis. Thus the only difference between the eye and gaze frames is the angle Kappa between the eye's optic and visual axes.

The key purpose of defining the gaze frame is to obtain the direction of the gaze vector in space. The eye's location and direction of gaze define a line, and the gazepoint is computed by finding the intersection of that line and the viewing surface.

3.2.6 Coordinate Transformations

There are four key transformations between the above five coordinate transformations. Each transformation has six degrees of freedom: three offsets and three rotations. Once all 24 degrees of freedom are defined, it is possible to precisely transform points and vectors (i.e., eyeball locations, and gaze vectors) between the various frames and to compute the user's gazepoint accurately.

The linear offsets, or translations, between two coordinate frames are defined as $X_{offset}$, $Y_{offset}$ and $Z_{offset}$. Angular relationships between coordinate frames are defined by Euler angle transformations. The sequence of rotations for all forward coordinate transforms is "ThetaY," yaw (pan) about the y axis, "ThetaX," pitch (tilt) about the x' axis after the yaw rotation, and "ThetaZ," roll (bank) about the z'' axis after the yaw and pitch rotations. All rotations are positive right handed about their respective axes.

1. World-to-Gimbal Transform

Translations: The world-to-gimbal translation is the vector from the center of the world frame (e.g., the center of the computer monitor screen) to the center of the gimbal-base frame (which is also the center of the camera sensor). The world-to-gimbal angles define the orientation of the gimbal base with respect to the world frame.

In one embodiment of the eyefollower, it is assumed that the gimbal base position and angles are fixed within the world coordinate frame, so the world-to-gimbal transform is constant during eyetracking operation. The world-to-gimbal angles and translations are inferred during a "Full" calibration process (discussed below).

2. Gimbal-to-Camera Transform

The gimbal is designed so that the center of the camera sensor remains at the origin of the gimbal base frame as the gimbal pivots, so the gimbal-to-camera translations are all zero. The gimbal has a controllable yaw and pitch. The eyefollower gimbals are physically nested such that the yaw and pitch angles correspond directly to Euler angles as defined in the above convention. The gimbal has no roll pivot, so the gimbal-to-camera's Euler roll angle is always zero. (There is, however, "apparent" roll due to yaw and pitch.)

The gimbal yaw and pitch angles are measured by sensors in the control loop. The gimbal-to-camera transform is computed from the measured gimbal angles each camera field.

3. Camera-to-Eye Transform

The camera-to-eye translation is the vector position of the eye's nodal point with respect to the center of the camera sensor. The camera-to-eye angles define the 3-D orientation of the eyeball with respect to the camera axes.

The eye's position and orientation are in constant motion with respect to the camera, and the camera-to-eye transform is computed from the results of the Eye Image Processing each camera field.

4. Eye-To-Gaze Transform

The gaze frame is centered at the eye's nodal point, as is the eye frame, so the eye-to-gaze translations are all zero. The eye-to-gaze yaw and pitch angles correspond to the eye's anatomical angle Kappa. The gaze frame's x and y axes are defined by a sequence of two rotations from the eye frame to the gaze frame: 1) a yaw rotation about the y axis, and 2) a pitch rotation about the x axis. The eye-to-gaze roll angle is defined to be zero.

Being based on fixed anatomical properties of the eye, the eye-to-gaze transform is constant for an individual user. The eye-to-gaze rotations (which are equivalent to Kappa) are computed during the "Individual" calibration procedure (discussed below).

Forward and Inverse Transforms

For nomenclature purposes, the progression of transformations beginning with the world frame and working toward the gaze frame, are defined as the "forward" transforms. The reverse progression of transforms, beginning with the gaze frame and working back to the world frame, is defined as the "inverse" transforms.

4. Exemplary Explicit Calibration

To perform accurate predictions of a person's gazepoint on a computer monitor from the camera's image of the eye, the eyegaze system's explicit raytrace algorithms depend on two sets of parameter values that are not known at the time of the system design, and thus are obtained during calibration procedures. These two sets of parameters are anatomical information about the eye regarding the direction of gaze with respect to the eye's observable features, and geometric information about the position and orientation of the gimbal base with respect to the world coordinate frame.

Relevant information on the eye includes radius of curvature of the cornea, corneal flattening toward the outer edges, corneal astigmatism, and the magnitude and direction of the angle Kappa between the visual and optic axes. Relevant information on the gimbal-base/monitor geometry includes 3-D positional offset of the camera from the display origin, and 3-D angular orientation of the camera with respect to the display screen.

The values of all these parameters are inferred from eyegaze calibration procedures.

4.1 The Calibration Procedure

The system infers the values of unknown gazepoint-prediction parameters by performing a calibration procedure where the subject sequentially looks at a series of nine calibration dots displayed at different locations on the screen. In one embodiment of the present invention, the calibration program begins, the user signals the system that he is ready to start "following the dot" by making the eye gesture of looking directly at the camera. The calibration program then displays the first calibration point. At each calibration point, the system waits for the gaze to move away from the old location, waits for the gaze to move approximately to the new location, waits for the eye to fixate, measures the glint-pupil vector data during the fixation period, automatically moves to the next calibration point, and automatically retakes calibration points if there are inconsistencies. After the successful collection of all the calibration points, the calibration program uses a regression procedure to estimate the calibration parameters.

4.2 Explicit Calibration Program

From the user's point of view, the eyegaze system's calibration procedure is the same for both the explicit and lumped-parameter raytrace algorithms. Thus, the user procedure does not change with the addition of the eyefollower. The user simply follows the dot with his eyes as it moves to several locations on screen.

The internal structure of the calibration program, however, does change with the addition of the eyefollower. The explicit calibration program now consists of two separate modes: the "full calibration" mode, which should be run by a qualified eyegaze technician, and the "individual calibration" mode which is run by each individual user.

4.2.1 Full Calibration Mode

In the full calibration mode, the key objective is to estimate the monitor-to-gimbal Transform coefficients. In this mode, the calibration program computes both the monitor-to-gimbal coefficients and the eye parameters, but only the monitor-to-gimbal coefficients are of interest.

A qualified eyegaze technician should perform the full calibration procedure. Another embodiment of the present invention is a method to exercise the full range of the eyefollower. To exercise the full range of the eyefollower, the operator moves his head to six locations near each edge of the permissible head range: far right, far left, top, bottom, closest in, and farthest out. At each of these six locations, he follows the full dot-sequence described above.

Given this extensive data collection in the full calibration mode, eye-image data is collected for the eye looking over all ranges of the screen space, for the head located at all extremes of the permissible head volume. Thus, the matrix inversion within the parameter regression algorithm is maximally constrained and the resulting parameter values are optimized.

4.2.2 Individual Calibration Mode

In the individual calibration mode, the key objective of the calibration procedure is to estimate the eye parameters of the individual user. In this mode, it is assumed that the gimbal/monitor transform coefficients are already known from a previously performed full calibration. The user need only follow a single sequence of dots and he need not move his head, although he is free to do so.

4.2.3 Explicit Regression Methods

All modes of the eyegaze calibration procedures can use explicit regression methods to determine best estimates of the calibration parameter values (Seber, 1989).

5. Eyefollower Performance Tests

In a particular implementation of the present invention, the eyefollower met or exceeded all performance goals. The total head tracking volume was 18 inches side to side, ten inches forward and back, and eight inches up and down. The system tracked head velocities of 10 in/sec, twice the target goal, and tracked head accelerations of 35 in/sec/sec, exceeding the goal of 30 in/sec/sec.

The performance of the focus-range tracking is particularly noteworthy. The asymmetric aperture method, analyzing the corneal reflection image from the eye, provides a highly reliable indication of the camera's focus-range error with respect to the corneal surface. In turn, the use of this focus-range error in the lens control loop results in rapid and smooth eyefollower responses to the user's forward and backward head motions.

5.1 Dynamic Focus Control Tests

Another embodiment of the present invention is a closed-loop focus control system that responds to forward and backward head motion. A lens of a camera moves in dynamic response to head motion. The head motion test pattern is similar to that used in testing a focus measurement with a fixed lens except that the amplitudes of the head motion are larger, and the final oscillations grow in magnitude to exercise the full range of the focus tracker.

Figure 4:
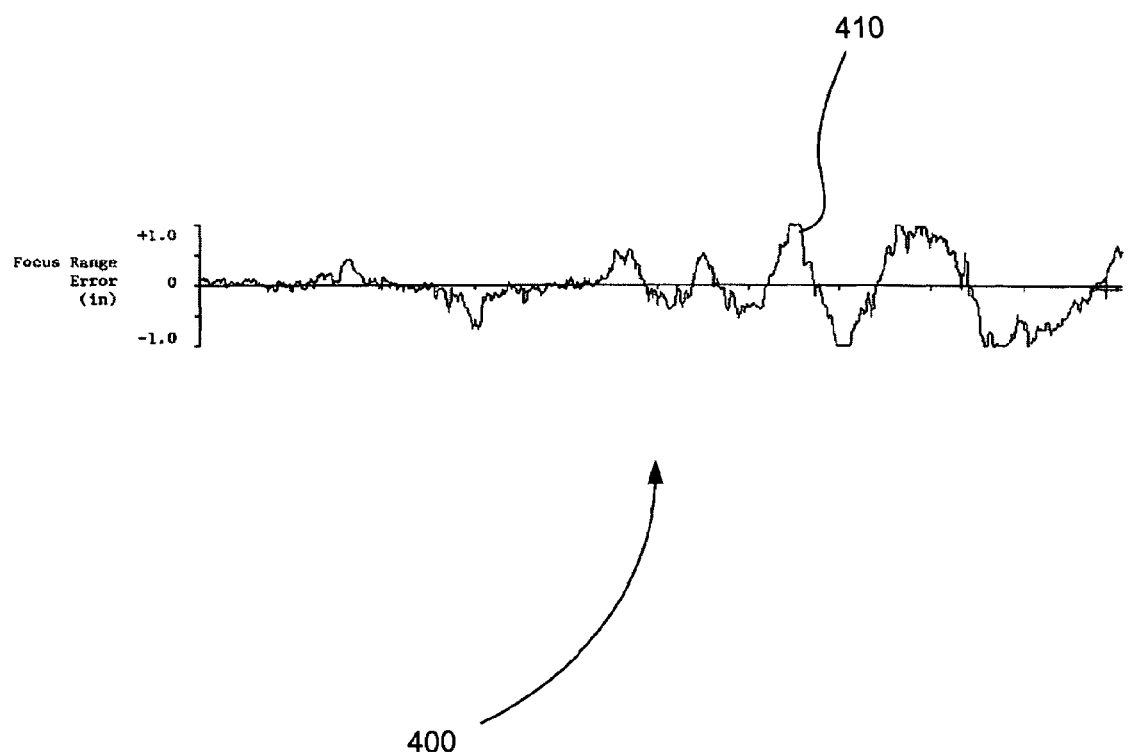
FIG. 4 is an exemplary plot of a focus-range error for a closed-loop focus control system that responds to forward and backward head motion, in accordance with an embodiment of the present invention.

FIG. 4 is an exemplary plot 400 of a focus-range error 410 for a closed-loop focus control system that responds to forward and backward head motion, in accordance with an embodiment of the present invention.

Figure 5:
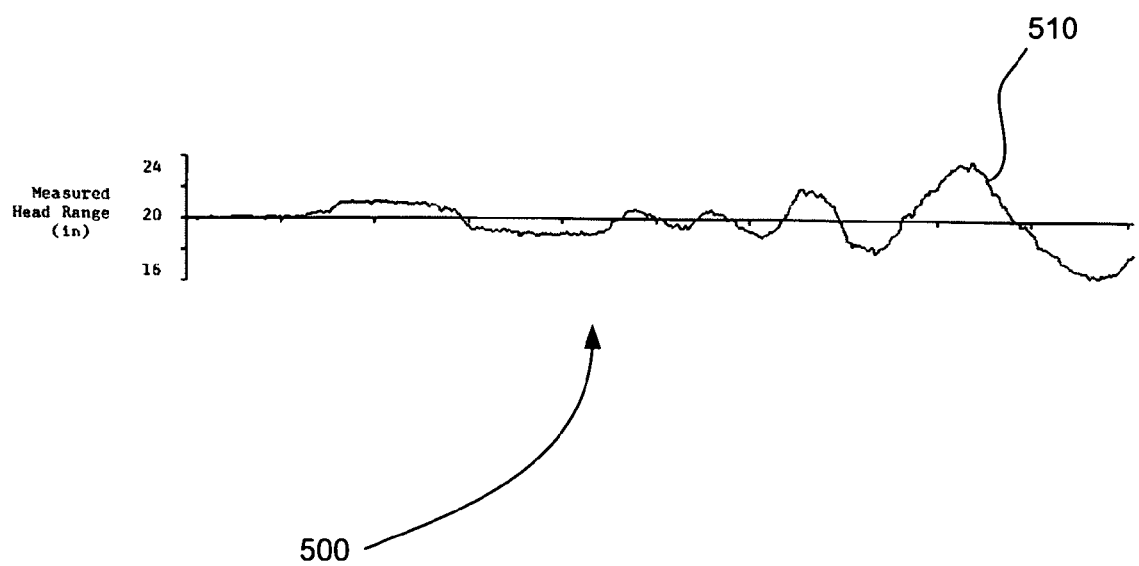
FIG. 5 is an exemplary plot of a head-range for a closed-loop focus control system that responds to forward and backward head motion, in accordance with an embodiment of the present invention.

FIG. 5 is an exemplary plot 500 of a head-range 510 for a closed-loop focus control system that responds to forward and backward head motion, in accordance with an embodiment of the present invention. The system tracked 8 inch head motions at speeds of up to 5 inches per second and accelerations up to 30 inches per second squared. As seen in FIG. 4, focus-range errors are held within 0.2 inches when the head is relatively still and within 1.0 inch during large motions. The noise in the measurement of the focus-range error is approximately a quarter inch RMS. Since the range from the camera to the eye is the sum of the lens' focus range and the focus-range error, the accuracy of the eye-range measurement is on the order of a quarter inch.

5.2 Gazepoint Tracking Accuracy

Because of the variable camera/monitor geometry, the addition of the eyefollower to the eyegaze system can reduce the overall gazepoint tracking accuracy. With the eyefollower, average tracking errors increase approximately 15 to 20%, from about 0.25 inches RMS to 0.29 to 0.30 inches RMS. Remarkably, however, the tracking accuracy remains fairly constant over the entire tracking volume, which is 1000 times the size of the head tracking volume without the eyefollower.

The major sources of eyefollower-induced gazepoint tracking errors are the sensors that measure the gimbal yaw, gimbal pitch and camera lens extension. Improved sensor design in the eyefollower can significantly reduce eyefollower-induced gazepoint tracking error.

Figure 6:
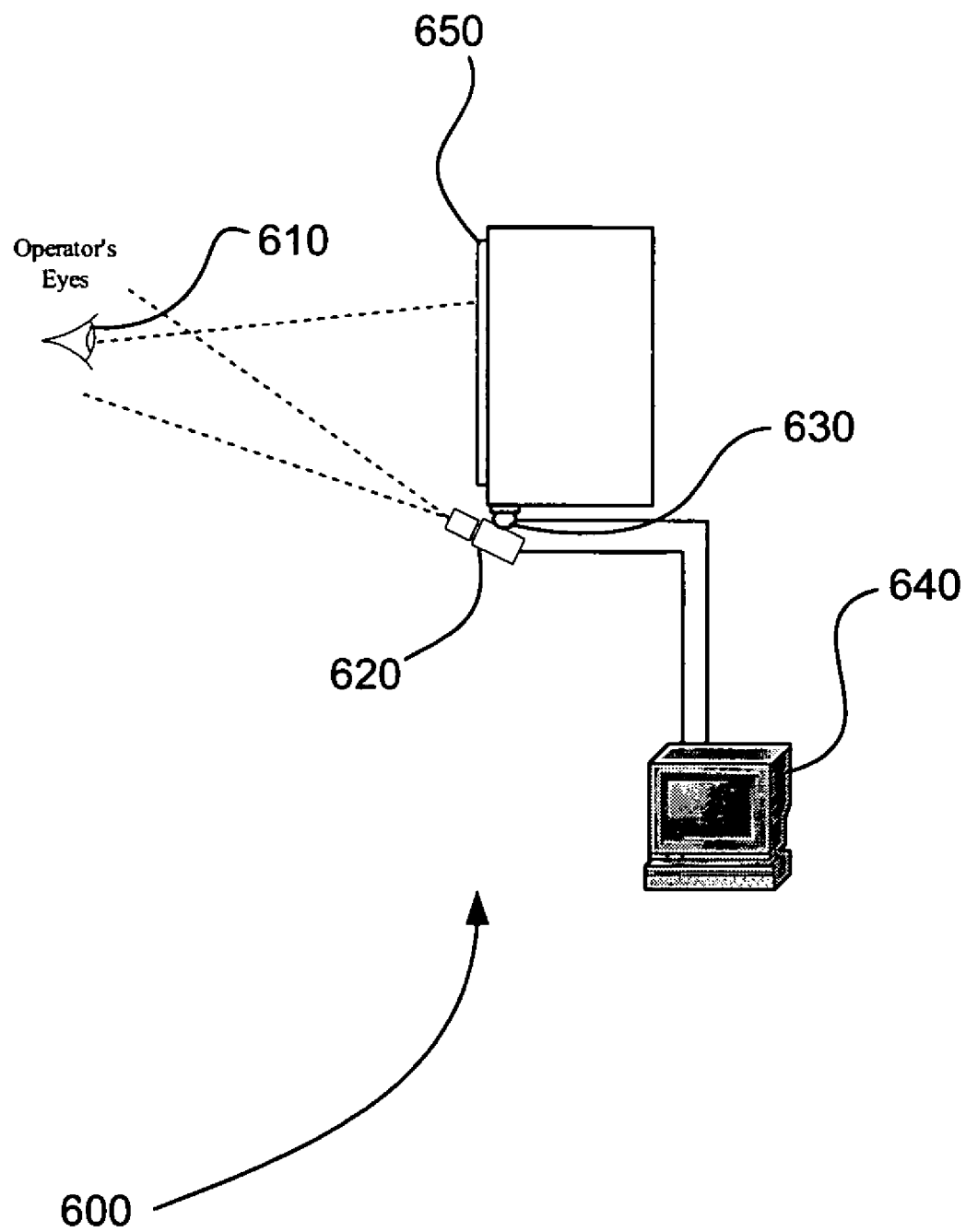
FIG. 6 is a schematic diagram of a system for computing a first gaze axis of an eye in a first coordinate system, in accordance with an embodiment of the present invention.

FIG. 6 is a schematic diagram of a system 500 for computing a first gaze axis of an eye 610 in a first coordinate system, in accordance with an embodiment of the present invention. Camera 620 focuses on eye 610 and moves to maintain the focus on eye 610 as eye 610 moves in the first coordinate system. Gimbal 630 is connected to camera 620. Gimbal 630 is used to move camera 620. Processor 640 is connected to camera 620 and gimbal 630 such that processor 640 controls the focus of camera 620, controls movement of gimbal 630, and measures a first location of camera 620 in the first coordinate system. Processor 640 measures a second location of eye 610 and a gaze direction of eye 610 within a second coordinate system. Processor 640 computes a second gaze axis within the second coordinate system from the second location and the gaze direction. Processor 640 computes the first gaze axis from the second gaze axis and the first location of eye 610 with the first coordinate system using a first coordinate transformation.

In another embodiment of the present invention, the first coordinate system is a world coordinate system and the second coordinate system is a coordinate system of camera 620.

In another embodiment of the present invention, the world coordinate system is defined with respect to two-dimensional screen 650 of a display.

In another embodiment of the present invention, processor 640 computes a gaze point of eye 610 as a point on screen 650 where the first gaze axis intersects the screen.

In another embodiment of the present invention, the first coordinate transformation comprises a second coordinate transformation between the coordinate system of camera 620 and a coordinate system of gimbal 630 and a third coordinate transformation between the coordinate system of gimbal 630 and the world coordinate system.

In another embodiment of the present invention, processor 640 measures the first location of camera 620 in the first coordinate system using camera orientation sensors.

In another embodiment of the present invention, processor 640 measures the second location of eye 610 and the gaze direction of eye 610 within the second coordinate system using an asymmetric aperture method.

In another embodiment of the present invention, processor 640 measures the second location of eye 610 and the gaze direction of eye 610 within the second coordinate system by measuring a second gaze direction of eye 610 within a coordinate system of eye 610, selecting a point on the second gaze direction as a third location of eye 610 within the coordinate system of eye 610, converting the second gaze direction to the gaze direction and the third location to the second location using a second coordinate transformation.

Figure 7:
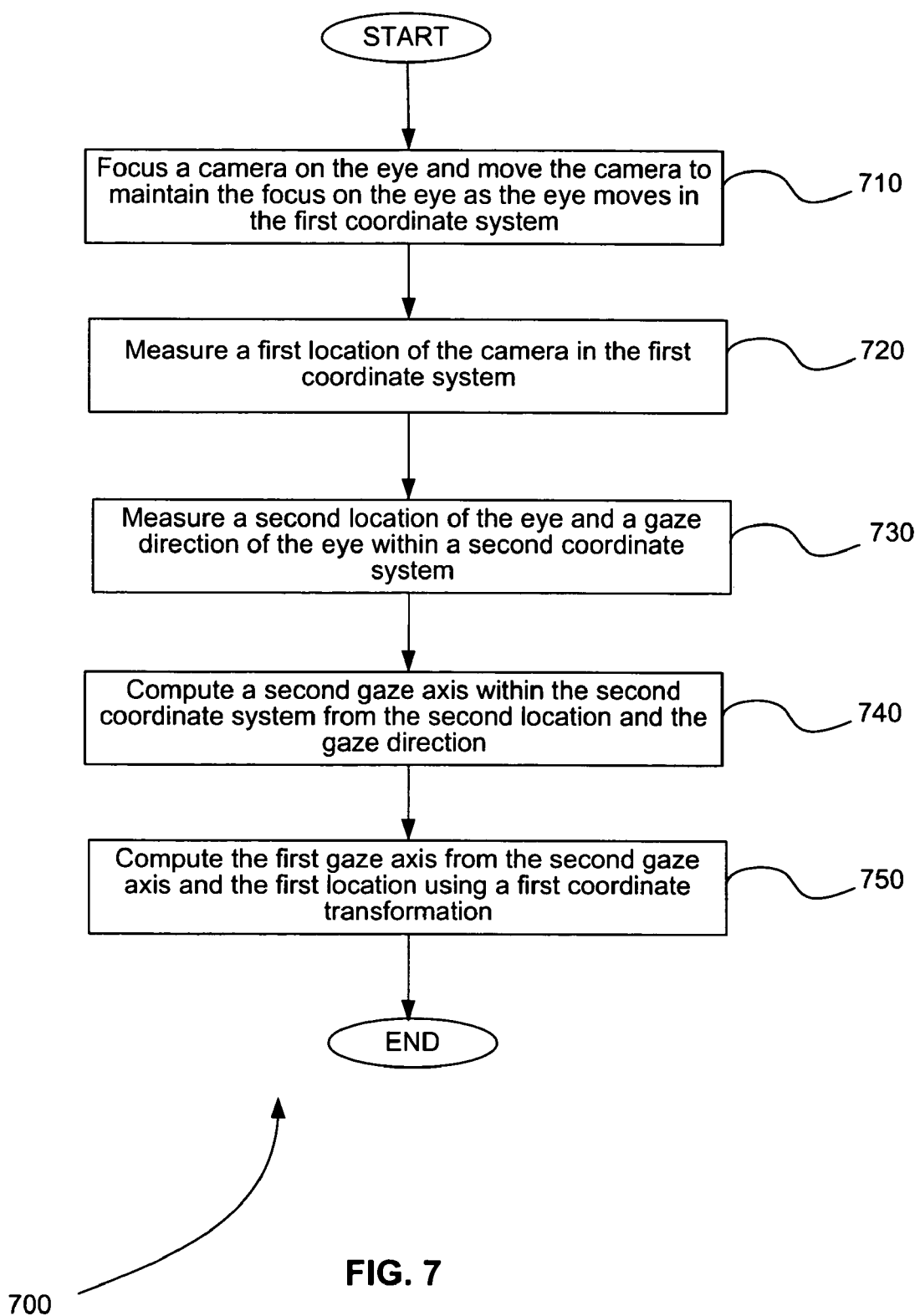
FIG. 7 is a flowchart showing a method for computing a first gaze axis of an eye in a first coordinate system, in accordance with an embodiment of the present invention.

FIG. 7 is a flowchart showing a method 700 for computing a first gaze axis of an eye in a first coordinate system, in accordance with an embodiment of the present invention.

In step 710 of method 700, a camera is focused on the eye and moved to maintain the focus on the eye as the eye moves in the first coordinate system.

In step 720, a first location of the camera in the first coordinate system is measured.

In step 730, a second location of the eye and a gaze direction of the eye within a second coordinate system is measured.

In step 740, a second gaze axis within the second coordinate system is computed from the second location and the gaze direction.

In step 750, the first gaze axis is computed from the second gaze axis and the first location using a first coordinate transformation.

In another embodiment of the present invention, the first coordinate system is a world coordinate system and the second coordinate system is a coordinate system of the camera.

In another embodiment of the present invention, the world coordinate system is defined with respect to a two-dimensional screen of a display.

In another embodiment of the present invention, a gaze point of the eye is computed as a point on the screen where the first gaze axis intersects the screen.

In another embodiment of the present invention, the use of the first coordinate transformation includes performing a second coordinate transformation between the coordinate system of the camera and a coordinate system of a gimbal connected to the camera and performing a third coordinate transformation between the coordinate system of gimbal and the world coordinate system and wherein gimbal is used to move the camera.

In another embodiment of the present invention, the first location of the camera in the first coordinate system is measured using camera orientation sensors.

In another embodiment of the present invention, the second location of the eye and the gaze direction of the eye are measured within the second coordinate system using an asymmetric aperture method.

In another embodiment of the present invention, the second location of the eye and the gaze direction of the eye are measured within the second coordinate system by measuring a second gaze direction of the eye within a coordinate system of the eye, selecting a point on the second gaze direction as a third location of the eye within the coordinate system of the eye, converting the second gaze direction to the gaze direction and the third location to the second location using a second coordinate transformation.

Figure 8:
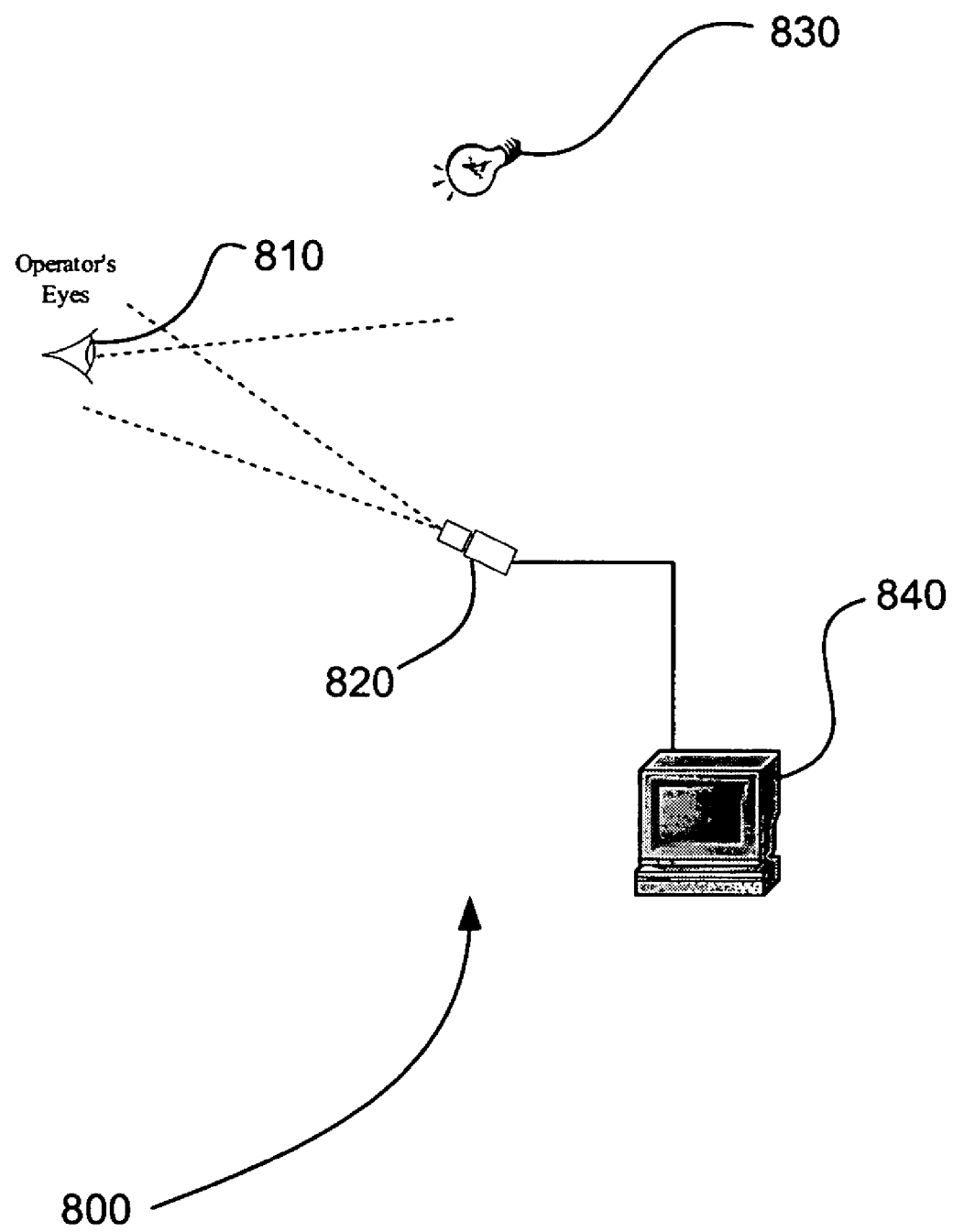
FIG. 8 is a system for determining a three-dimensional location and orientation of an eye within a camera frame of reference, in accordance with an embodiment of the present invention.

FIG. 8 is a system 800 for determining a three-dimensional location and orientation of an eye 810 within a camera frame of reference, in accordance with an embodiment of the present invention. System 800 includes a camera 820, an illuminator 830, and a processor 840. Camera 820 captures an image of eye 810. Illuminator 830 generates a reflection off of a corneal surface of eye 810. Processor 840 computes a first two-dimensional location of a pupil reflection image and a corneal reflection image from the image of eye 810. Processor 840 predicts a second two-dimensional location of a pupil reflection image and the corneal reflection image as a function of a set of three-dimensional position and orientation parameters of eye 810 within the camera frame of reference. Processor 840 iteratively adjusts the set until the first two-dimensional location is substantially the same as the second two-dimensional location. The set of three-dimensional position and orientation parameters of eye 810 within the camera frame of reference then define the three-dimensional location and orientation of eye 810.

In another embodiment of the present invention, processor 840 predicts the second two-dimensional location using optical ray-tracing functions that model eye shape and camera optics.

In another embodiment of the present invention, the optical ray-tracing functions used by processor 840 employ an ellipsoidal model for the corneal surface of eye 810, the ellipsoidal model further including a nominal radius of curvature at a center of a cornea, a parameter defining a flattening of a corneal curvature toward corneal edges, and a parameter defining a degree of astigmatism on the corneal surface.

In another embodiment of the present invention, the optical ray-tracing functions used by processor 840 employ an ellipsoidal model for the corneal surface of eye 810, the ellipsoidal model further including a nominal radius of curvature at a center of a cornea, a parameter defining a flattening of a corneal curvature toward corneal edges, and a parameter defining an angle of astigmatism on the corneal surface.

In another embodiment of the present invention, the optical ray-tracing functions used by processor 840 account for a refraction of a pupil image that results from the camera viewing a pupil of through a curved corneal surface.

In accordance with an embodiment of the present invention, instructions adapted to be executed by a processor to perform a method are stored on a computer-readable medium. The computer-readable medium can be a device that stores digital information. For example, a computer-readable medium includes a read-only memory (e.g., a Compact Disc-ROM ("CD-ROM") as is known in the art for storing software. The computer-readable medium can be accessed by a processor suitable for executing instructions adapted to be executed. The terms "instructions configured to be executed" and "instructions to be executed" are meant to encompass any instructions that are ready to be executed in their present form (e.g., machine code) by a processor, or require further manipulation (e.g., compilation, decryption, or provided with an access code, etc.) to be ready to be executed by a processor.

In the foregoing detailed description, systems and methods in accordance with embodiments of the present invention have been described with reference to specific exemplary embodiments. Accordingly, the present specification and figures are to be regarded as illustrative rather than restrictive.

The foregoing disclosure of the preferred embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

What is claimed is:

1. A system for computing a first gaze axis of an eye in a first coordinate system, comprising:
    a camera, wherein the camera focuses on the eye and moves to maintain the focus on the eye as the eye moves in the first coordinate system;
    a gimbal, wherein the gimbal is connected to the camera and wherein the gimbal is used to move the camera, and
    a processor,
        wherein the processor is connected to the camera and the gimbal such that the processor controls the focus, controls movement of the gimbal, and measures a first location of the camera in the first coordinate system;
        wherein the processor measures a second location of the eye and a gaze direction of the eye within a second coordinate system;
        wherein the processor computes a second gaze axis within the second coordinate system from the second location and the gaze direction; and
        wherein the processor computes the first gaze axis from the second gaze axis and the first location using a first coordinate transformation that comprises one or more rotational parameters.

2. The system of claim 1, wherein the first coordinate system is a world coordinate system and the second coordinate system is a coordinate system of the camera.

3. The system of claim 2, wherein the world coordinate system is defined with respect to a two-dimensional screen of a display.

4. The system of claim 3, wherein the processor computes a gaze point of the eye as a point on the screen where the first gaze axis intersects the screen.

5. The system of claim 2, wherein the first coordinate transformation comprises a second coordinate transformation between the coordinate system of the camera and a coordinate system of the gimbal and a third coordinate transformation between the coordinate system of the gimbal and the world coordinate system.

6. The system of claim 1, wherein the processor measures the first location of the camera in the first coordinate system using camera orientation sensors.

7. The system of claim 1, wherein the processor measures the second location of the eye and the gaze direction of the eye within the second coordinate system using an asymmetric aperture method.

8. The system of claim 1, wherein the processor measures the second location of the eye and the gaze direction of the eye within the second coordinate system by measuring a second gaze direction of the eye within in a coordinate system of the eye, selecting a point on the second gaze direction as a third location of the eye within the coordinate system of the eye, converting the second gaze direction to the gaze direction and the third location to the second location using a second coordinate transformation.

9. A method for computing a first gaze axis of an eye in a first coordinate system, comprising:
    focusing a camera on the eye and moving the camera to maintain the focus on the eye as the eye moves in the first coordinate system;
    measuring a first location of the camera in the first coordinate system;
    measuring a second location of the eye and a gaze direction of the eye within a second coordinate system;
    computing a second gaze axis within the second coordinate system from the second location and the gaze direction; and
    computing the first gaze axis from the second gaze axis and the first location using a first coordinate transformation that comprises one or more rotational parameters.

10. The method of claim 9, wherein the first coordinate system is a world coordinate system and the second coordinate system is a coordinate system of the camera.

11. The method of claim 10, wherein the world coordinate system is defined with respect to a two-dimensional screen of a display.

12. The method of claim 11, further comprising computing a gaze point of the eye as a point on the screen where the first gaze axis intersects the screen.

13. The method of claim 10, wherein the first coordinate transformation comprises performing a second coordinate transformation between the coordinate system of the camera and a coordinate system of a gimbal connected to the camera and performing a third coordinate transformation between the coordinate system of the gimbal and the world coordinate system and wherein the gimbal is used to move the camera.

14. The method of claim 9, wherein measuring the first location of the camera in the first coordinate system further comprises using camera orientation sensors.

15. The method of claim 9, wherein measuring the second location of the eye and the gaze direction of the eye within the second coordinate system further comprises using an asymmetric aperture method.

16. The method of claim 9, wherein measuring the second location of the eye and the gaze direction of the eye within the second coordinate system further comprises measuring a second gaze direction of the eye within in a coordinate system of the eye, selecting a point on the second gaze direction as a third location of the eye within the coordinate system of the eye, converting the second gaze direction to the gaze direction and the third location to the second location using a second coordinate transformation.

* * * * *